United States Patent
Denoux et al.

(10) Patent No.: US 7,955,525 B2
(45) Date of Patent: Jun. 7, 2011

(54) PEROXIDE REDUCTION IN FUNCTIONALIZED VEGETABLE OILS

(75) Inventors: Michael G. Denoux, Metairie, LA (US); Ritchie Tregre, Vacherie, LA (US); Garrett Mineo, Marrero, LA (US)

(73) Assignee: Galata Chemicals, LLC, Southbury, CT (US)

( * ) Notice: Subject to any disclaimer, the term of this patent is extended or adjusted under 35 U.S.C. 154(b) by 0 days.

(21) Appl. No.: 12/859,427

(22) Filed: Aug. 19, 2010

(65) Prior Publication Data

US 2010/0317874 A1 Dec. 16, 2010

Related U.S. Application Data

(62) Division of application No. 11/634,745, filed on Dec. 5, 2006.

(51) Int. Cl.
*C09K 15/32* (2006.01)
*C07F 9/02* (2006.01)
*C07D 301/36* (2006.01)
*C07D 303/02* (2006.01)

(52) U.S. Cl. ............... 252/400.2; 252/400.24; 554/78; 549/202; 568/8

(58) Field of Classification Search ......... 252/400.2, 252/400.24; 554/78; 549/202; 568/8
See application file for complete search history.

(56) References Cited

U.S. PATENT DOCUMENTS

| | | | | |
|---|---|---|---|---|
| 2,822,368 | A | * | 2/1958 | Rowland et al. ............ 549/540 |
| 2,951,052 | A | * | 8/1960 | Darby ........................ 524/114 |
| 2,997,454 | A | * | 8/1961 | Hecker et al. .............. 524/147 |
| 3,637,555 | A | | 1/1972 | Marinacci et al. |
| 3,661,825 | A | * | 5/1972 | Horvath et al. ............ 524/114 |
| 3,886,104 | A | | 5/1975 | Borman et al. |
| 4,032,481 | A | * | 6/1977 | Pillar ........................... 521/56 |
| 4,159,261 | A | * | 6/1979 | Dieckmann ................ 524/180 |
| 4,209,468 | A | | 6/1980 | Shulman |
| 4,839,188 | A | | 6/1989 | Wheeler et al. |
| 5,874,643 | A | | 2/1999 | Mineo et al. |
| 5,936,048 | A | | 8/1999 | Oishi et al. |
| 5,973,082 | A | | 10/1999 | Elmore |
| 6,548,609 | B2 | * | 4/2003 | Ramirez-de-Arellano-Aburto et al. .......................... 525/530 |
| 2002/0183428 | A1 | * | 12/2002 | Hachiya et al. ............ 524/315 |
| 2006/0201056 | A1 | | 9/2006 | Jordan |
| 2007/0173626 | A9 | | 7/2007 | Geiger et al. |

OTHER PUBLICATIONS

International Preliminary Report on Patentability mailed May 3, 2009 in PCT/US2007/023983.
International Search Report mailed on May 27, 2008 in PCT/US2007/023983.

* cited by examiner

*Primary Examiner* — Lorna M Douyon
*Assistant Examiner* — Tanisha Diggs
(74) *Attorney, Agent, or Firm* — Dilworth IP, LLC

(57) ABSTRACT

Disclosed is an oil composition wherein the oil contains measurable amounts of peroxide resulting from peroxidation, and also includes an effective amount of a peroxide-reducing phosphorous compound, preferably an alkyl/aryl substituted phosphite compound or phosphinic acid ($H_3PO_2$) and its derivatives.

13 Claims, No Drawings

PEROXIDE REDUCTION IN FUNCTIONALIZED VEGETABLE OILS

CROSS-REFERENCE TO RELATED APPLICATIONS

This application is a Division of Ser. No. 11/634,745, filed Dec. 5, 2006.

FIELD OF INVENTION

This invention relates to a method for the reduction of residual peroxides in vegetable oils. More particularly, epoxidized vegetable oils having unacceptably high levels of peroxides are effectively treated to reduce peroxides using a hydrocarbyl substituted phosphite compound preferably alkyl/aryl substituted phosphite compounds.

BACKGROUND OF THE INVENTION

Functionalized vegetable oils have been extensively used for various applications, such as coatings, inks and agrochemicals. They can also be functionalized by epoxidation with organic peracids or $H_2O_2$. These epoxidized vegetable oils show excellent utility as inexpensive, renewable materials for industrial applications.

The most commonly utilized epoxidized oil is epoxidized soybean oil (ESO), that is soybean oil whose double bonds have been converted to epoxy (oxirane) groups. These products are used as plasticizers for poly(vinyl chloride) (PVC) polymers and copolymers. The ESO also serves to stabilize the vinyl resin. Epoxidized linseed oil (ELO) is also used with bisphenol epoxy resins to increase the flexibility of amine cured epoxy polymers. Epoxidized linseed oil can be further functionalized by reacting with such materials as acrylic acid. The acrylated oil is used in ultraviolet (uv) curing inks. Epoxidized and other types of functionalized vegetable oils have many other industrial, non-food applications which are sensitive to the presence of residual peroxide which can have undesirable effects in the final products. Thus it is desirable to reduce the residual peroxide levels to a minimum for optimum consistency of properties of the epoxidized oil products.

Hydrogen peroxide is widely used in the commercial epoxidation of vegetable and other plant-derived oils due to the capability of hydrogen peroxide to react with unsaturated substances in the oils to yield oxirane (1,2-epoxy) compounds and/or 1,2-glycols, dependent upon reaction conditions. These reactions, known as epoxidation and hydroxylation, respectively, are similar in many respects including the similarity of preparative methods; and the ease of transition from 1,2-epoxy compounds, for example, to the corresponding glycols. Available methods for preparing epoxy compounds and glycols, via reaction of a peroxygen compound with an olefinic material, include reactions utilizing alkaline hydrogen peroxide, hydrogen peroxide in anhydrous tertiary alcohols, hydrogen peroxide in the presence of light, and organic peracids. These synthetic routes are all useable to make epoxidized vegetable oils. At the conclusion of the epoxidation reaction, residual peroxide and peroxide derived radicals may unavoidably remain in the finished epoxidized vegetable oil. Many end uses find elevated levels of residual peroxide to have potentially detrimental effects on the final product and processes of making the final product. It would be desirable to have a simple method for removing or deactivating residual peroxide.

Vegetable oils which are polyunsaturated, especially safflower oil, sunflower seed oil, soybean oil and corn oil are particularly susceptible to hydroperoxide formation. Polyunsaturated fatty acids in vegetable oils, particularly linolenic esters in soybean oil, are especially sensitive to oxidation. A wide variety of naturally occurring oils and fats contain a mixture of olefinic compounds which vary in unsaturation and hence oxidizability from the singly unsaturated oleic to the polyconjugated oleostearic esters. This deterioration is generally due to their tendency to absorb or react with oxygen, and the observed rancidity results primarily from the products formed during oxidation. These products generally include unwanted peroxides, aldehydes, ketones and acids.

Aldehydes have been recognized for many years as the chemical agents responsible for deterioration of oils. These products have been shown to be derived from initially formed hydroperoxide. The primary initial products of the autoxidation of fatty acid esters, the hydroperoxides, appear to be odorless and flavorless. However, a host of carbonyl compounds, acids, and other products are formed, through decomposition and further oxidation of the hydroperoxides. Oxygen from the air first reacts with the unsaturated fatty acid esters at or adjacent to the double bonds to form hydroperoxides which then decompose to yield aldehydes having the pungent odor and flavor of rancid fats. Oxidation is catalyzed by light and metals such as copper or iron and is accelerated by heat. It would be desirable to reduce or eliminate the hydroperoxides to stop the subsequent reactions from occurring. There are uses for some of the vegetable oils that can accept the presence of hydrocarbyl phosphites. It has been found that the phosphites are effective in reduction of peroxide (and hydroperoxide) levels in vegetable oils in addition to the epoxidized vegetable oils.

BRIEF DESCRIPTION OF THE INVENTION

The advantages of the invention may be obtained by incorporating into a vegetable or plant-derived oil, preferably an epoxidized vegetable oil an effective amount of a hydrocarbyl phosphite represented by the general formula:

(I)

where $R^1$, $R^2$, $R^3$ are independently selected from a bond, hydrogen, aryl and alkyl hydrocarbon groups. $R^1$, $R^2$, $R^3$ may be independently selected from aryl and alkyl hydrocarbon groups of from $C_1$ to $C_{100}$. Aryl groups may include phenyl or naphthyl groups further substituted by $C_1$ to $C_{20}$ branched or straight chain alkyl or aryl groups. Such substituted aryl also includes an aryl moiety in which a hydrogen has been replaced by an alkoxy radical, a thioalkyl radical, a halogen or other substituent which, itself, will not react with oxygen to produce undesirable hydroperoxide compounds.

Preferred alkyls for $R^1$, $R^2$, $R^3$ are $C_1$ to $C_{20}$ branched or straight chain substituents. The diester and triester phosphites are more preferred. The tri substituted phosphites where $R^1$, $R^2$, $R^3$ are the same substituents are more easily manufactured and as such are slightly preferred. Specific preferred phosphites include triisodecyl phosphite, tris nonylphenol phosphite, diphenyl 2-ethylhexyl phosphite, triphenyl phosphite, triethyl phosphite, trimethyl phosphite, tris(2,4-di-t-butylphenyl)phosphite, trilauryl phosphite, and tristearyl phosphite.

Exemplary phosphites include: triisodecyl phosphite, tris nonylphenol phosphite, diphenyl 2-ethylhexyl phosphite, tris (nonyl phenyl)phosphite, tris(butyl phenyl)phosphite, trimethyl phosphite, triethyl phosphite, tris (2 ethylhexyl)phosphite, triisopropyl phosphite, triisoctyl phosphite, diisoctyl, phosphite, distearyl phosphite, triisodecyl phosphite, triisoctyl phosphite, trilauryl phosphite, tristearyl phosphite, diphenyl phosphite, triphenyl phosphite, diphenyl isodecyl phosphite, diphenyl isooctyl phosphite, phenyl isodecyl phosphite, dilauryl phosphite, di-tridecyl phosphite, ethylhexyl diphenyl phosphite, and diisooctyl octylphenyl phosphite. Preferred organic phosphites are trioctyl, tridecyl, tridodecyl, tritridecyl, tripentadecyl, trioleyl, tristearyl, triphenyl, tricresyl, tris(nonylphenyl), tris(2,4-tert-butylphenyl) and tricyclohexyl phosphite. Other suitable phosphites are various mixed aryl dialkyl or alkyl diarylphosphites, such as phenyl dioctyl, phenyl didecyl, phenyl didodecyl, phenyl ditridecyl, phenyl ditetradecyl, phenyl dipentadecyl, octyl diphenyl, decyl diphenyl, undecyl diphenyl, dodecyl diphenyl, tridecyl diphenyl, tetradecyl diphenyl, pentadecyl diphenyl, oleyl diphenyl, stearyl diphenyl and dodecyl bis(2,4-di-tert-butylphenyl)phosphite.

One embodiment is a method for reducing the peroxide content of an epoxidized vegetable oil to a predetermined lower peroxide level comprising adding 0.01 to 10 weight percent of a hydrocarbyl phosphite of structure (I) to an epoxidized vegetable oil having a measurable amount of peroxide contained therein and mixing said hydrocarbyl phosphite into the epoxidized vegetable oil for a time sufficient to reduce the peroxide to said predetermined lower peroxide level. The foregoing method may optionally include the additional preliminary steps of epoxidizing a vegetable oil using hydrogen peroxide or an organic peracid to form an epoxidized vegetable having a quantity of residual peroxide above said predetermined lower peroxide level.

Another embodiment is an epoxidized vegetable oil composition comprising an epoxidized vegetable oil containing measurable amounts of peroxide having incorporated therein a peroxide-reducing effective amount of a hydrocarbyl phosphite represented by structure (I).

Yet another embodiment is a vegetable oil composition comprising a vegetable oil containing peroxide in an amount above a desired minimum level and a peroxide-reducing effective amount of a hydrocarbyl phosphite incorporated therein, said hydrocarbyl phosphite being represented by the general formula (I).

Still another embodiment is a method for reducing the peroxide content of vegetable oil to a predetermined lower peroxide level comprising: adding 0.01 to 10 weight percent of hydrocarbyl phosphite represented by general formula (I) to a epoxidized vegetable oil having a measurable amount of peroxide contained therein; and mixing said hydrocarbyl phosphite into the epoxidized vegetable oil for a time sufficient to reduce the peroxide to said predetermined lower peroxide level In each embodiment set forth above, the hydrocarbyl phosphite is represented by the general formula (I):

wherein $R^1$, $R^2$, $R^3$ are independently selected from a bond, hydrogen, aryl and alkyl hydrocarbon groups may be further defined by any of the following preferred subgenus and species representations:

1. alkyl hydrocarbon group is a $C_1$ to $C_{20}$ branched or straight chain alkyl;
2. the aryl group is a phenyl or naphthyl group optionally substituted by $C_1$ to $C_{20}$ branched or straight chain alkyl or aryl groups;
3. $R^1$, $R^2$, $R^3$ are the same hydrocarbyl group;
4. $R^1$ is hydrogen and $R^2$, $R^3$ are independently alkyl or aryl;
5. $R^1$, $R^2$, $R^3$ are all alkyl from $C_1$ to $C_{50}$;
6. $R^1$, $R^2$, $R^3$ are all aryl;
7. $R^1$ is alkyl and $R^2$, $R^3$ are aryl;
8. at least one of $R^1$, $R^2$, $R^3$ is a substituted aryl moiety in which a hydrogen has been replaced by an alkoxy radical, a thioalkyl radical, a halogen or other substituent which will not react with oxygen to produce undesirable hydroperoxide compounds;
9. the epoxidized vegetable oil is selected from the group consisting of soybean oil, sunflower seed oil, corn oil, coconut oil, hydrogenated soybean oil, groundnut oil, olive oil, hydrogenated cottonseed oil, rapeseed oil, palm olein, palm oil, hydrogenated rapeseed oil, and linseed oil; and
10. the epoxidized vegetable oil is selected from the group consisting of epoxidized soybean oil, epoxidized octyl tallate ester, and epoxidized linseed oil.

In still another embodiment of the invention, the phosphorous compound utilized to reduce the peroxide in vegetable oils or epoxidized vegetable oil is hypophosphorous acid (HPA), also known as phosphinic acid, and the CAS Number 6303-21-5, having a chemical formula $H_3PO_2$. In each instance this compound is mentioned it will be understood to include $H_3PO_2$ and its derivatives, preferably esters

DETAILED DESCRIPTION OF THE INVENTION

Vegetable oils have been extensively used for various non-food applications, such as coatings, inks, and agrochemicals. They can also be functionalized by epoxidation with organic peracids or $H_2O_2$. Such epoxidized vegetable oils show excellent promise as inexpensive, renewable materials for industrial applications. Epoxidized soybean oil, that is soybean oils whose double bonds have been converted to epoxy (oxirane) groups are used as plasticizers for poly(vinyl chloride) (PVC) polymers and copolymers that also serve to stabilize the vinyl resin. Epoxidized oils such as linseed oil may be used with bisphenol epoxy resins to increase the flexibility of amine cured epoxy polymers. Epoxidized oils such as linseed oil can be further functionalized by reacting with acrylic acid. The acrylated oil is used in ultraviolet (uv) curing inks. Other examples of suitable epoxidized alkyl fatty acid esters are epoxidized propylene glycol dioleate and epoxidized 2-ethylhexyltallate or epoxidized octyltallate ester. Typical products are available commercially under the Drapex® product line and a trademark of Chemtura Corporation of Middlebury, Conn. The term vegetable oil as used herein is meant to include these tallate oils since they are plant derived oils.

Typical Synthesis of Epoxidized Vegetable Oils

For synthesis of epoxidized soybean oil (ESO), a solution of soybean oil (100 g, 0.14 mol), glacial acetic acid (25.2 g, 0.42 mol), ion exchange resin (25 g) and toluene (40 g) were placed in a round, four-necked 500 mL flask equipped with a mechanical stirrer, thermometer sensor and reflux condenser. The mixtures were heated to a constant temperature of 55° C. Then, 30% $H_2O_2$ (79.4 g, 0.7 mol) was added slowly from a separatory funnel and allowed to react at 55° C. for 7 hours. After the reaction was complete, the crude product was filtered and washed with distilled water repeatedly until pH 7.0. The oil phase was dried with anhydrous sodium sulfate and then filtered. Finally, the toluene was removed in a vacuum oven at 80° C.: yield 89%.

Epoxidized castor oil (ECO) was synthesized from castor oil (91.8 g, 0.14 mol), glacial acetic acid (21.0 g, 0.35 mol), ion exchange resin (23 g), toluene (40 g) and 30% H2O2 (56.7 g, 0.5 mol) similarly to the synthesis of epoxidized soybean oil: yield 84%.

The term "oil" as used herein can be naturally occurring or synthetically produced having unsaturation in its structure and meet any one of the following criteria:
1. It contains oleic acid.
2. It contains palmitic acid.
3. It contains mixtures of mixed triglycerides.
4. It contains $C_{14}$-$C_{18}$ saturated fat molecules and $C_{14}$-$C_{24}$ unsaturated fat molecules.

Specifically included are the many vegetable oils, both naturally occurring and functionalized forms, such as hydrogenated or epoxidized vegetable oils and others. These include, soybean oil, sunflower seed oil, corn oil, coconut oil, hydrogenated soybean oil, groundnut oil, olive oil, cottonseed oil, rapeseed oil, and palm oil.

Oleic acid (cis-octadec-9-enoic acid, $CH_3$—$[CH_2]_7$—CH=CH—$[CH_2]_7$—COOH is widespread in natural fatty acids; in very many oils it forms more than 30 percent of the total fatty acids, and up to the present it has been found absent from no natural fat or phosphatide. The most common constituent of all natural fats is thus an unsaturated (mono-ethenoid), normal aliphatic acid with a content of eighteen carbon atoms and the unsaturated linking between the ninth and tenth carbon atoms of the chain. Many other unsaturated acids, mono- or poly-ethenoid, are also found in fats, and of these quite a number have features of chemical structure which bear similarity, close or remote, to that of oleic acid. Other unsaturated acids, however, seem to be quite different from oleic acid and its structurally related acids in the arrangement of their unsaturated linkings. None of the other unsaturated acids are so uniformly distributed, or so prominent as a whole, in natural fats as oleic acid; but two at least appear to be nearly as widespread, namely, octadeca-9,12-dienoic acid (linolenic acid or related forms) and lenolinic acid.

Saturated normal aliphatic acids are, of course, widely distributed in natural fats. Here the characteristic member of the group is palmitic acid, $CH_3[CH_2]_{14}COOH$; this acid occurs in very many fats, in which it may contribute from 15 to 50 percent of the total fatty acids like oleic acid, it is completely absent from few, if any, of the natural fats. The fatty acid mixtures are combined as triglycerides in fats from different regions of the vegetable and animal kingdoms. They are woven into molecules of triglycerides in vegetable or animal fat. Natural fats should be defined, in fact, as mixtures of mixed triglycerides.

This invention relates to the use of phosphite compounds which are especially useful for reducing levels of peroxide and also for prohibiting the build-up of hydroperoxides in vegetable oils and functionalized vegetable oils as epoxidized soybean oil.

The term "vegetable oil" is also understood to include oils derived from vegetative sources such the tall oil ester and oleic acid esters derived from vegetative materials which are commercially available as unfunctionalized oil materials, exemplified by such materials as iso-octyl oleate, iso-octyl ester of tall oil fatty acids, 1,2 -Propylene glycol dioleate, 1,2-Propylene glycol diester of tall oil fatty acids, 1,3-Butylene glycol diester of tall oil fatty acids, Pentaerythritol tetraester of tall oil fatty acids or as functionalized forms such as epoxidized octyl tallate ester, epoxidized 2-ethylhexyltallate and epoxidized propylene glycol dioleate By "peroxide reducing effective amount" herein is meant an amount which substantially reduces the peroxide or hydroperoxide in vegetable oils, an amount in the range of about 0.001 to about 10.0 percent by weight. Preferably the amount used will be about 0.01 to about 2.0 and more preferably 0.1 to about 1.0 percent by weight. The exact amount depends generally on the amount of peroxides present in the vegetable oils. Where the phosphite is added primarily to prevent formation of hydroperoxides, the effective amounts or generally less than the amounts used for peroxide reducing amounts.

By "comprising" herein is meant that various other compatible ingredients may be present in the compositions in such a proportion as will not adversely affect the stability and the peroxide reducing effectiveness of the phosphite. The term "comprising" thus encompasses and includes the more restrictive terms "consisting of" and "consisting essentially of" within its scope.

Types of Oils-Physical Properties

TABLE 1

Viscosity of Deodorized Oils and Fats at Different Temperatures[a]

| Oil or Fat | IV[d] | Viscosity,[b] mPa · s (=cP) | | | Constants[c] | |
| --- | --- | --- | --- | --- | --- | --- |
| | | 20° C. | 40° C. | 60° C. | a | B |
| soybean oil | 134 | 60 | 28 | 15 | −0.073 | 46.6 |
| medium-chain triglycerides | 0 | | 21 | 11 | −0.306 | 50.1 |
| sunflower seed oil | 132 | 63 | 29 | 16 | −0.038 | 44.8 |
| corn oil | 122 | 70 | 30 | 16 | −0.142 | 49.9 |
| coconut oil | 9 | | 27 | 14 | −0.242 | 51.0 |

TABLE 1-continued

Viscosity of Deodorized Oils and Fats at Different Temperatures[a]

| Oil or Fat | Viscosity,[b] mPa · s (=cP) | | | | Constants[c] | |
|---|---|---|---|---|---|---|
| | IV[d] | 20° C. | 40° C. | 60° C. | a | B |
| hydrogenated soybean oil, mp 28° C. | 101 | | 33 | 18 | −0.148 | 51.1 |
| Butterfat | 38 | | 34 | 17 | −0.151 | 51.2 |
| groundnut oil | 89 | 81 | 36 | 19 | −0.080 | 50.5 |
| Olive oil | 83 | 82 | 35 | 17 | −0.102 | 50.1 |
| hydrogenated cottonseed oil, mp 32° C. | 76 | | 45 | 23 | −0.166 | 55.9 |
| rapeseed oil | 104 | 93 | 41 | 21 | −0.023 | 50.1 |
| lard olein | 73 | | 36 | 18 | −0.151 | 51.9 |
| Palm olein | 64 | | 37 | 19 | −0.145 | 52.2 |
| Palm oil | 51 | | 37 | 19 | −0.192 | 53.8 |
| Lard | 63 | | 36 | 19 | −0.068 | 48.2 |
| hydrogenated rapeseed oil, mp 32° C. | 81 | | 49 | 24 | −0.140 | 56.0 |

[b]Standard deviation of replicates 1%.
[c]Constants in the equation $\log \rho = a + 10^6 b t^{-3}$ (t = ° C.).
[d]IV = iodine value, a measure of unsaturation.
Source for Table 4: G. L. Hasenhuettl, Consultant, Kirk-Othmer Encyclopedia of Chemical Technology Copyright © 2005 by John Wiley & Sons, Inc. 10.1002/0471238961.0601201908011905.a01.pub2 Article Online Posting Date: Feb. 18, 2005

Working Examples

This experimental section demonstrates specific methods and compositions which reduce the peroxide value (PV) of both epoxidized and unepoxidized vegetable oils. The oils were treated with small amounts of several types of triester phosphites. In some experiments the samples were just mixed at various temperatures and then allowed to stand. In others, they were heated under vacuum. The phosphite treatments significantly reduced the PV's of the oil and in some cases reduced material with an initial PV greater than 15 meq/kg to below 1 meq/kg (essentially zero). The phosphite treatment also improves the stability at high temperatures.

Experimental Methods

One hundred gram batches of epoxidized soybean oil (ESO) were treated with various amounts of phosphites and mixed for 30 minutes after gently warming between 140° F. and 160° F. Once mixed, the effects on the peroxide content were determined. The peroxide content was run using AOCS Method Cd 8b-90 and reported as the "initial peroxide value" (PV) in meq/1 000 g. The actual initial PV value prior to addition of the phosphite is substantially equal to the 15.16 of Comparative A. Some of the above batches, which were stored at 160° F., were observed over time to monitor the effects of Phosphite on the PV. The PV as shown in Table 2 did not drop appreciably after the initial reduction.

Phosphite Treatment of Epoxidized Soybean Oil (ESO)

TABLE 2

| | Phosphite | Phosphite % | Initial PV (meg/1000 g) | 4 Day PV |
|---|---|---|---|---|
| Comparative A | Untreated ESO | None | 15.16 | 13.03 |
| Example 1 | Triisodecyl Phosphite | 0.3% | 3.32 | 2.98 |
| Example 2 | Tris Nonylphenol Phosphite | 0.4% | 4.53 | 3.80 |
| Example 3 | Liquid aryl alkyl phosphite | 0.4% | 4.07 | 3.61 |
| Example 4 | Diphenyl 2-Ethylhexyl Phosphite | 0.1% | 6.66 | Not run |

The ESO treated with 0.3% Triisodecyl Phosphite from Example 1 was analyzed for typical properties before and after the addition of TDP. Only minor changes in properties were observed as shown in Table 3.

TABLE 3

Effects on Epoxidized Soybean Oil Product Characteristics

| | ESO | Refractive Index | Specific Gravity | Epoxy Value | Iodine Value | Acid Value | Moisture |
|---|---|---|---|---|---|---|---|
| Example. 5 | Treated | 1.4707 | 0.9925 | 7.01 | 1.59 | 0.43 | 0.037 |
| Comparative B | Untreated | 1.4708 | 0.9931 | 7.02 | 1.52 | 0.44 | 0.029 |

To determine how the reduction proceeded at room temperature and to determine the effect of concentration on peroxide reduction, 100 grains of ESO was treated with increasing amounts of Triisodecyl Phosphite (TDP) at room temperature, mixed for 5 minutes, and analyzed for PV. The reduction occurred rapidly at room temperature and was directly proportional to the amount of phosphite added. Comparative C shows the control level of peroxide and each of Examples 6-9 shows the improvement in peroxide reduction is proportional to phosphite level with the range tested, 0.1 to 0.4% by weight.

TABLE 4

Rate of Peroxide Value Reduction at Room Temperature

| | Percent Phosphite-Triisodecyl Phosphite | Peroxide Value (PV) |
|---|---|---|
| Comparative C | None | 15.16 |
| Example 6 | 0.1% | 10.64 |
| Example 7 | 0.2% | 5.99 |
| Example 8 | 0.3% | 2.14 |
| Example 9 | 0.4% | 0.16 |

Effectiveness on Other Vegetable Oils

The effects of Triisodecyl Phosphite (TDP) on residual Peroxides were also confirmed on soybean oil, epoxidized octyltallate ester (EOT), and epoxidized linseed oil (ELO) by treating 100 grams of oil and mixing for five minutes at room temperature. Examples 10-12 show excellent reduction of peroxide levels.

TABLE 5

Effect of Phosphites on Soybean Oil and other Epoxidized Oils

|  |  | Percent TDP Phosphite | Before Treatment | After Treatment |
|---|---|---|---|---|
| Example 10 | Soybean Oil | 0.1% | 2.45 | 0.57 |
| Example 11 | EOT | 0.4% | 20.80 | 6.63 |
| Example 12 | ELO | 0.1% | 1.26 | ND |

The results of using small amounts of phosphites (both alkyl and aryl) to reduce the residual peroxide content of vegetable oils and epoxidized vegetable oils were investigated. In all cases the peroxide value (PV) of vegetable oils and epoxidized vegetable oils were reduced. The amount of reduction was directly dependant on the amount of phosphite added. Reduction occurred rapidly at both room and elevated temperatures. Phosphites can reduce the PV to essentially zero, if a sufficient amount is added for the peroxide present, with little effect to the analytical properties of the product.

Peroxide Reduction Using Hypophosphorous Acid

One to two liter batches of epoxidized soybean oil (ESO) were treated with 0.1% of HPA (50% HPA in Water) and mixed for 30 to 60 minutes after gently warming between 130° F. and 150° F. Once mixed the effects on the peroxide content, as well as other characteristics, were determined. Standard methods for ESO analysis were used. The peroxide contents were run using AOCS Method Cd 8b-90 and reported as the peroxide value (PV) in meq/1000 g.

TABLE 6

HPA Treatment of Epoxidized Soybean Oil (ESO)

|  | PV (meq/1000 g) | APHA Color | Refractive Index | Specific Gravity | Acid Value | Epoxy Value | Iodine Value |
|---|---|---|---|---|---|---|---|
| Comparative D | 16.25 | 57 | 1.4710 | 0.9924 | 0.44 | 7.03 | 1.71 |
| Example 13 | 0.45 | 71 | 1.4711 | 0.9924 | 0.82 | 6.80 | 2.06 |
| Example 14 | 1.55 | 85 | 1.4710 | 0.9914 | 0.84 | 6.71 | 1.91 |
| Example 15 | 1.11 | 68 | 1.4712 | 0.9923 | 0.87 | 6.89 | 2.11 |
| Example 16 | 3.09 | 60 | 1.4714 | 0.9939 | 0.74 | 6.89 | 1.39 |
| Example 17 | 6.88 | 59 | 1.4713 | 0.9927 | 0.74 | 6.93 | 1.26 |

Samples of the batches of Examples 14, 17 and 18 were stored at ambient temperatures and were observed over time to monitor the effects of HPA on the PV. The PV continued to drop over time. Example 18 has a lower level of HPA added (0.05%) to evaluate effects of lower quantities of HPA efficacy in long term aging.

TABLE 7

Peroxide Value Reduction Over Time

| Batch | PV After Initial Treatment | 3 Days | 4 Days | 6 Days | 12 Days |
|---|---|---|---|---|---|
| Example 14 | 1.55 | 0.43 | 0.26 | 0.06 | 0.00 |
| Example 17 | 6.88 | 2.26 | 1.94 | 1.83 | 1.11 |

TABLE 7-continued

Peroxide Value Reduction Over Time

| Batch | PV After Initial Treatment | 3 Days | 4 Days | 6 Days | 12 Days |
|---|---|---|---|---|---|
| Example 18 (0.05% HPA) | 11.70 | N/A | 5.87 | 5.28 | 4.96 |

To monitor the effect temperature has on the rate of PV reduction, 1200 grams of ESO was treated with 0.1% HPA at room temperature, mixed for 15 min., and separated into three samples. Each sample was placed in ovens set to different temperatures. Higher temperature increased the rate of PV reduction.

TABLE 8

Effect of Temperature on the Rate of Peroxide Value Reduction

|  | 75° F. | 120° F. | 160° F. |
|---|---|---|---|
| 30 min. after treatment | 11.33 | 11.33 | 11.33 |
| 22 hrs. after treatment | 2.90 | 0.70 | 0.46 |

The effectiveness of HPA at 0.1% by weight on residual peroxides in other vegetable and plant-derived oils were also confirmed on unepoxidized soybean oil, epoxidized octyltallate (EOT), and epoxidized linseed oil (ELO) by treating 100 grams of oil and mixing for one minute at room temperature.

TABLE 9

Effect of HPA on Soybean Oil and other Epoxidized Oils

|  | Before Treatment | 2 Days After Treatment |
|---|---|---|
| Soybean Oil | 2.22 | 1.06 |
| EOT | 14.06 | 2.32 |
| ELO | 4.11 | 0.68 |

The results of using Hypophosphorous acid (HPA) to reduce the residual peroxide content of vegetable oils and epoxidized vegetable oils showed it to be effective. In all cases the peroxide value of vegetable oils and epoxidized vegetable oils were reduced by hypophosphorous acid (HPA). The amount of reduction is dependent on the amount of HPA added, the temperature and the material treated. The PV will continue to drop over time until the PV is fully reduced or the HPA is consumed.

Various changes and modifications to the examples and description can be made by one skilled in the art without departing from the invention as hereinafter claimed.

What is claimed is:

1. An oil composition consisting of an epoxidized vegetable oil having a measurable initial amount of peroxide and a peroxide-reducing effective amount of hypophosphorous acid or a hydrocarbyl phosphite, wherein said hydrocarbyl phosphite is represented by the general formula (I):

wherein $R_1$, $R_2$, and $R_3$ are independently selected from hydrogen, aryl and alkyl hydrocarbon groups.

2. The oil composition according to claim 1, wherein in the hydrocarbyl phosphite of formula (I) the alkyl hydrocarbon group is a $C_1$ to $C_{20}$ branched or straight chain alkyl group.

3. The oil composition according to claim 1, wherein in the hydrocarbyl phosphite of formula (I) the aryl group is a phenyl or naphthyl group optionally substituted by $C_1$ to $C_{20}$ branched or straight chain alkyl or aryl groups.

4. The oil composition according to claim 1, wherein in the hydrocarbyl phosphite of formula (I) $R_1$, $R_2$, and $R_3$ are the same hydrocarbyl group.

5. The oil composition according to claim 1, wherein in the hydrocarbyl phosphite of formula (I) $R_1$ is hydrogen and $R_2$ and $R_3$ are independently alkyl or aryl.

6. The oil composition according to claim 1, wherein in the hydrocarbyl phosphite of formula (I) $R_1$, $R_2$, and $R_3$ are all alkyl.

7. The oil composition according to claim 1, wherein in the hydrocarbyl phosphite of formula (I) $R_1$, $R_2$, and $R_3$ are all aryl.

8. The oil composition of claim 1, wherein in the hydrocarbyl phosphite of formula (I) $R_1$ is alkyl and $R_2$ and $R_3$ are aryl.

9. The oil composition according to claim 1, wherein in the hydrocarbyl phosphite of formula (I) at least one of $R_1$, $R_2$, and $R_3$ is a substituted aryl moiety in which a hydrogen has been replaced by an alkoxy radical, a thioalkyl radical, a halogen or other substituent which will not react with oxygen to produce undesirable hydroperoxide compounds.

10. The oil composition according to claim 1, wherein said epoxidized vegetable oil is selected from the group consisting of soybean oil, sunflower seed oil, corn oil, coconut oil, hydrogenated soybean oil, groundnut oil, olive oil, hydrogenated cottonseed oil, rapeseed oil, palm olein, palm oil, hydrogenated rapeseed oil, and linseed oil.

11. The oil composition according to claim 1, wherein said epoxidized vegetable oil is selected from the group consisting of soybean oil, linseed oil, and rapeseed oil.

12. The oil composition according to claim 1, wherein the epoxidized vegetable oil is selected from the group consisting of epoxidized soybean oil, epoxidized octyl tallate ester, epoxidized propylene glycol dioleate, epoxidized 2-ethylhexyl tallate, and epoxidized linseed oil.

13. The oil composition according to claim 1 wherein said hydrocarbyl phosphite is selected from the group consisting of triisodecyl phosphite, tris nonylphenyl phosphite, diphenyl 2-ethylhexyl phosphite, triphenyl phosphite, triethyl phosphite, trimethyl phosphite, tris(2,4-di-t-butylphenyl)phosphite, trilauryl phosphite, and tristearyl phosphite.

* * * * *